US00PP09981P

United States Patent [19]

Blough et al.

[11] Patent Number: Plant 9,981

[45] Date of Patent: Jul. 29, 1997

[54] RHODODENDRON PLANT NAMED 'PURPLE PASSION'

[75] Inventors: Robert L. Blough; Margaret A. Blough, both of Johnstown, Pa.

[73] Assignee: The Conard-Pyle Company, West Grove, Pa.

[21] Appl. No.: 651,360

[22] Filed: May 22, 1996

[51] Int. Cl.[6] ..... A01H 5/00

[52] U.S. Cl. ..... Plt./55

[58] Field of Search ..... Plt./55, 56, 57

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

A new and distinct variety of Rhodendron plant is provided that is believed to be a chance seedling of the 'Purple Splendour' variety (non-patented in the United States). Attractive large bright deep purple blossoms are formed that are highlighted with white and delicate maroon spots on the throat. A well-branched compact and vigorous growth habit is exhibited. The winter hardness is good in U.S.D.A. Zone 5 and the dark green foliage has shown disease resistance during observations to date. Additionally, the new variety exhibits a good aptitude for rooting from mature cuttings.

3 Drawing Sheets

SUMMARY OF THE INVENTION

The new variety of Rhododendron plant of the present invention was discovered during 1974 while growing in a cultivated area of our nursery at Johnstown, Pa., U.S.A. More specifically, the new variety was found and selected from among many other plants while growing at the same location as open-pollinated seedlings of the 'Purple Splendour' variety (non-patented in the United States). As indicated, the new variety is believed to trace its parentage to the 'Purple Splendour' variety and its different characteristics are of unknown causation. It was the goal of the selection program that resulted in the new variety to provide attractive new plants that are able to well tolerate the harsh winters of U.S.D.A. Zone 5 at Johnstown, Pa., U.S.A.

It was found that the new cultivar of the present invention exhibits the following combination of characteristics:

(a) forms attractive large bright deep purple blossoms with white highlighting and delicate maroon spots on the throat,
(b) forms a well-branched compact and vigorous growth habit,
(c) forms attractive dark green foliage,
(d) exhibits good winter hardiness, and
(e) exhibits a good aptitude for rooting from mature cuttings.

It was found that the new variety of the present invention exhibits excellent winter hardiness of the leaves and buds. Ten year-old test plants growing in the landscape at Johnstown, Pa., U.S.A. have satisfactorily withstood temperatures of −23° F. Also, the ability to form roots on mature cuttings is considered to compare favorably with other previously known varieties that commonly are propagated by this means.

It has been found at West Grove, Pa., U.S.A. that all of the characteristics of the new variety are strictly transmissible to the offspring created by the rooting of cuttings.

When compared to the 'Purple Splendour' variety, the new variety of the present invention has been found to exhibit blossoms that are of a considerably more intense and darker purple coloration, to form darker green foliage, to exhibit superior disease resistance, and to exhibit superior winter hardiness.

The new variety has been named 'Purple Passion' and is being marketed by The Conard-Pyle Company under the HIGHLAND trademark.

BRIEF DESCRIPTION OF THE PHOTOGRAPHS

The accompanying photographs show typical specimens of plant parts obtained from the new variety of Rhododendron plant of the present invention as depicted in color as true as is reasonably possible to make the same in color illustrations of this character. The plants were three years of age and were grown at West Grove, Pa., U.S.A. The photographs were prepared indoors during April 1996 following forcing employing eight weeks of cold storage of container grown plants that previously had been grown outdoors.

Figure 6:
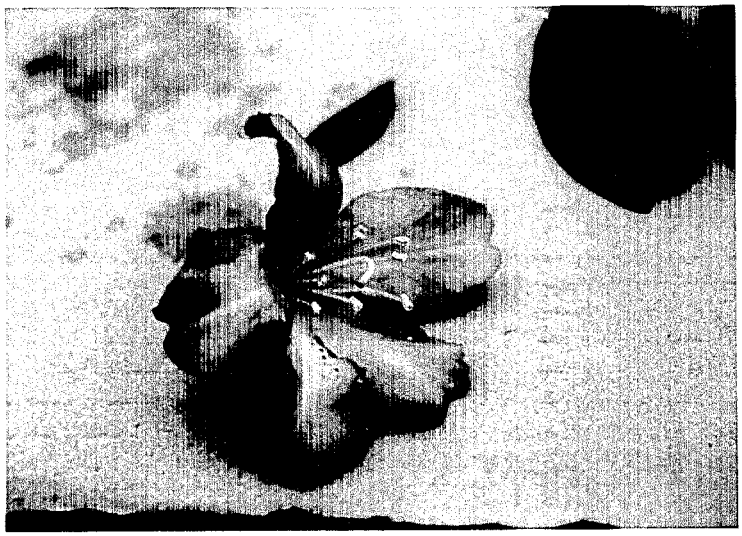

FIG. 6 illustrates a further typical floret of the new variety wherein the reproductive elements including near white stamens readily are visible. The broad funnel shape of the floret is depicted. The near white stamens contract nicely with the deep purple coloration of the lobes of the floret.

DETAILED DESCRIPTION

The following is a detailed description of the new Rhododendron variety of the present invention with color terminology in accordance with The R.H.S. Colour Chart of The Royal Horticultural Society, London, England. In some instances more general color terms are used that are to be accorded their customary dictionary significance. The description was prepared from the study of five year-old plants growing in a soilless medium during late May at West Grove, Pa., U.S.A.

Likely parentage: 'Purple Splendour' Rhododendron (non-patented in the United States).

Plant:

*Size.*—A field grown 10 to 15 year-old plant of the new variety when grown in U.S.D.A. Zone 5 is anticipated to assume a height of approximately 4 to 6 feet and a width of approximately 4 to 5 feet. Plants of the new variety when 3 years of age and grown in containers commonly exhibit a height of approximately 30 inches and a width of approximately 24 inches.

*Habit.*—Well-branched, vigorous, and compact.

Foliage:

*Type.*—Evergreen flowering shrub, semi-glossy lanceolate leaves with acute apex, and obtuse and entire margins.

*Size.*—Mature leaves growing midway up the stem commonly are approximately 9 to 12 cm. in length and approximately 3.7 to 4.9 cm. in width. Average leaf dimensions commonly are approximately 10.75 cm. in length and approximately 4.3 cm. in width.

Figure 1:
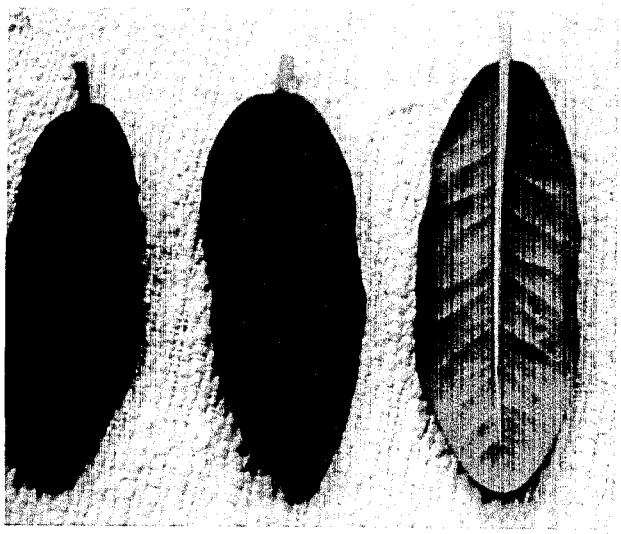
FIG. 1 illustrates specimens of three mature leaves of the new variety with the upper surface being shown at the left and center and the under surface being shown at the right.
Figure 2:
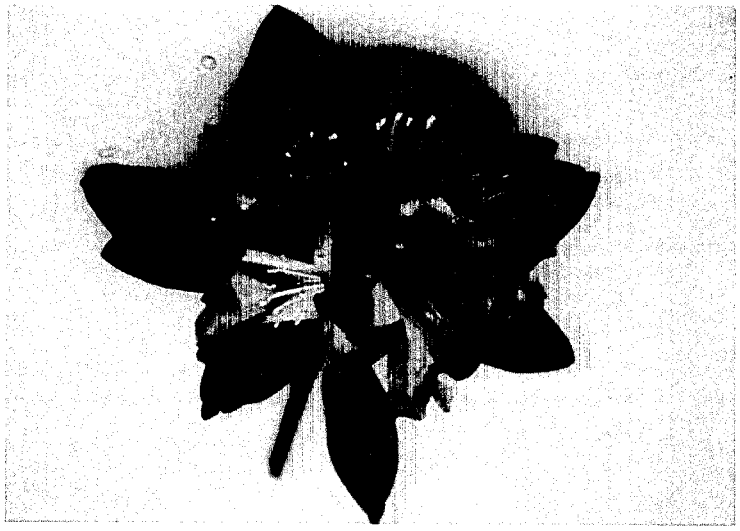
FIG. 2 illustrates a typical flower truss of the new variety with the upper foliage surfaces being depicted.
Figure 3:
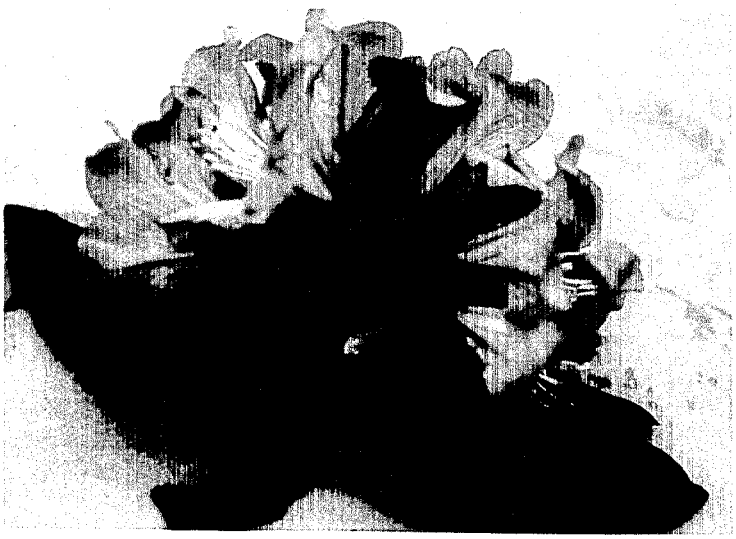
FIG. 3 illustrates a typical flower truss of the new variety from the side wherein some of the corolla have been removed so as to reveal the attachment of the corolla.

*Color.*—Dark green, Green Group 139A on the upper surface, and lighter green, Yellow-Green Group 146C on the under surface. See particularly FIG. 1, as well as the other figures where foliage is visible.

Branches:

*Color.*—Sheele's Green, Green Group 143C on mature one year-old wood, and Yellow-Green Group 145A on mature wood formed during current year.

Flowers:

*Period.*—Blooms approximately May 20th when cultured at U.S.D.A. Zone 5 Johnstown, Pa., USA.

*Truss shape.*—Generally as a ball.

*Corolla shape.*—As a broad funnel as illustrated in FIG. 6.

*Number of lobes.*—Five lobes per floret.

*Margin of lobes.*—Some waviness.

*Fragrance.*—None.

*Truss size.*—Commonly approximately 13.5 to 18 cm. in diameter, and approximately 9 cm. in height.

*Corolla per truss.*—Commonly approximately 12 to 16.

*Corolla size.*—Approximately 5 cm. in length and approximately 7.5 cm. in width.

*Calyx size.*—Approximately 2 mm. in length.

Figure 4:
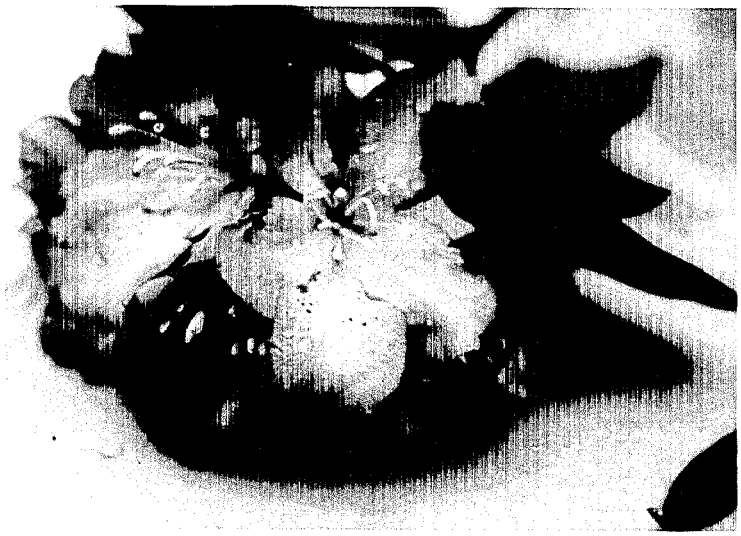
FIG. 4 illustrates a further typical flower truss of the new variety wherein the upper and under surfaces of the foliage also are visible, as well as the reproductive elements.
Figure 5:
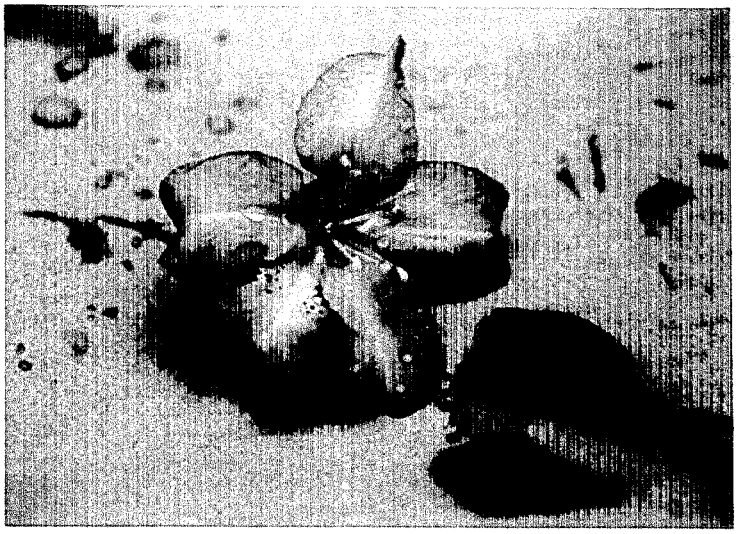
FIG. 5 illustrates a typical floret of the new variety together with unopened flower buds.

*Color.*—Buds: Purple Group 78B tipped with Purple Group 79C. Inside flower: Purple Group 78B commonly with white highlighting and delicate maroon spots on the throat. The spots, as illustrated in FIG. 4, often are concentrated towards the centers of the petals and commonly are Purple Group 77A with a halo of Red-Purple Group 72A sometimes being present around such spots. Outside flower: Purple-Violet Group 82A. Fully open flower: Commonly Purple-Violet Group 82A edged with Purple Group 77A. Calyx: Yellow-Green Group 144B and blushed with Red-Purple Group 72A. Stamens: Bright, and near white in coloration.

Winter hardiness: Has survived harsh winters in U.S.D.A. Zone 5 at Johnstown, Pa., U.S.A.

Disease resistance: During observations to date the foliage has been disease resistant.

We claim:

1. A new and distinct variety of Rhodendron plant, characterized particularly as to novelty by the following combination of characteristics:

(a) forms attractive large bright deep purple blossoms with white highlighting and delicate maroon spots on the throat, (b) forms a well-branched compact and vigorous growth habit, (c) forms attractive dark green foliage, (d) exhibits good winter hardiness, and (e) exhibits a good aptitude for rooting from mature cuttings.

substantially as herein shown and described.

* * * * *